United States Patent
Leone et al.

(10) Patent No.: US 11,382,961 B2
(45) Date of Patent: Jul. 12, 2022

(54) METABOLIC THERAPY FOR OXIDATIVE STRESS IN THE BRAIN THROUGH TARGETED NEURONAL CATABOLISM OF N-ACETYL-ASPARTIC ACID

(71) Applicant: ROWAN UNIVERSITY, Glassboro, NJ (US)

(72) Inventors: Paola Leone, Cherry Hill, NJ (US); Jeremy Francis, Cherry Hill, NJ (US)

(73) Assignee: ROWAN UNIVERSITY, Glassboro, NJ (US)

( * ) Notice: Subject to any disclaimer, the term of this patent is extended or adjusted under 35 U.S.C. 154(b) by 423 days.

(21) Appl. No.: 16/508,870

(22) Filed: Jul. 11, 2019

(65) Prior Publication Data

US 2020/0171134 A1 Jun. 4, 2020

Related U.S. Application Data

(63) Continuation of application No. 15/644,313, filed on Jul. 7, 2017, now Pat. No. 10,391,153, which is a continuation of application No. 13/906,171, filed on May 30, 2013, now Pat. No. 9,700,604.

(60) Provisional application No. 61/653,087, filed on May 30, 2012.

(51) Int. Cl.
| | | |
|---|---|---|
| *A61K 38/50* | (2006.01) | |
| *A61K 35/30* | (2015.01) | |
| *A61K 38/52* | (2006.01) | |
| *C12N 15/86* | (2006.01) | |

(52) U.S. Cl.
CPC .............. *A61K 38/50* (2013.01); *A61K 35/30* (2013.01); *A61K 38/52* (2013.01); *C12N 15/86* (2013.01); *C12Y 305/01015* (2013.01); *C12N 2750/14141* (2013.01)

(58) Field of Classification Search
None
See application file for complete search history.

(56) References Cited

U.S. PATENT DOCUMENTS

| | | |
|---|---|---|
| 2007/0026452 A1 | 2/2007 | Matalon et al. |
| 2008/0219971 A1 | 9/2008 | Smith et al. |

FOREIGN PATENT DOCUMENTS

| | | |
|---|---|---|
| WO | 9102796 A1 | 3/1991 |
| WO | 9509174 A1 | 4/1995 |
| WO | 2010071454 A1 | 6/2010 |

OTHER PUBLICATIONS

Blesa, et al. (2015) "Oxidative Stress and Parkinson's disease", Frontiers in Neuroanatomy, 9: Article 91, 9 pages. (Year: 2015).*

Percario, et al. (2020) "Oxidative Stress in Parkinson's Disease: Potential Benefits of Antioxidant Supplementation", Hindawi, article 2360872, 23 pages, (Year: 2020).*

Bankiewcz et al. "Long-term clinical improvement in MPTP-lesioned primates after gene therapy with AAV-hAADC." Molecular Therapy 14(4): 564-570 (2006).

Mandel et al. "Recombinant adeno-associated viral vectors as therapeutic agents to treat neurological disorders." Molecular Therapy 13(3): 463-483 (2006).

Surmeier et al. "What causes the death of dopaminergic neurons in Parkinson's disease?." Progress in Brain Research 183: 59-77 (2010).

Ahmed, et al., "Gene Therapy for Canavan's Disease Takes a Step Forward", Mol Therapy, vol. 21, No. 3, 2013, pp. 505-506.

Janson, et al., "Clinical Protocol Gene Therapy of Canavan Disease: AAV-2 vector for neurosurgical delivery of aspartoacylase gene (ASPA) to the human brain", Human Gene Therapy, vol. 13, No. 11, 2012, pp. 1391-1412.

Leone, et al., "Aspartoacylase Gene Transfer to the Mammalian Central Nervous System with Therapeutic Implications for Canavan Disease", Annals of Neurol, vol. 48, No. 1, 2000, pp. 27-38.

Leone, et al., "Long-Term Follow-Up After Gene Therapy for Canavan Disease", Science Translational Medicine, vol. 4, No. 165, Dec. 19, 2012, pp. 1-26.

Maarouf, et al., "Molecular Differences and Similarities Between Alzheimer's Disease and the 5XFAD Transgenic Mouse Model of Amyloidosis", Biochemistry Insights, vol. 6, 2013, pp. 1-7.

McPhee, et al., "Immune Responses to AAV in a Phase I Study for Canavan Disease", J Gene Med, vol. 8, No. 5, 2006, pp. 577-588.

Namboodiri, et al., "Canavandisease and the role of N-acetylaspartate in myelin synthesis", Mol & Cell Endocrin, vol. 252, 2006, pp. 516-523.

Surendran, et al., "Upregulation of aspartoacylase activity in the duodenum of obesity induced diabetes mouse implications on diabetic neuropathy", Biochem Biophys Res Comm, vol. 345, No. 3, May 11, 2006, pp. 973-975.

Zaroff, et al., "Transcriptional regulation of N-acetylaspartate metabolism in the 5xFAD model of Alzheimer's disease: Evidence for neuron-glia communication during energetic crisis", Mol Cell Neurosci, vol. 65, 2015, pp. 143-152.

Agrawal et al. "Cell-cycle kinetics and VSV-G pseudotyped retrovirus-mediated gene transfer in blood-derived CD34+ cells." Experimental Hematology 24(6): 738-747(1996).

(Continued)

*Primary Examiner* — Robert M Kelly
(74) *Attorney, Agent, or Firm* — Nixon Peabody LLP; Shayne Y. Huff; Ronald I. Eisenstein

(57) ABSTRACT

The present invention provides a novel method of treatment for treating brain disorders that manifest oxidative stress by providing targeted populations of neurons with the ability to catabolize the acetylated amino acid derivative, N-acetylaspatic acid (NAA) and further supply extraphysiological levels of ATP to neurons via the targeted expression of the NAA catabolic enzyme aspartoacylase (ASPA) in neurons and astrocytes.

14 Claims, 9 Drawing Sheets

Specification includes a Sequence Listing.

(56) References Cited

OTHER PUBLICATIONS

Capecchi. "High efficiency transformation by direct microinjection of DNA into cultured mammalian cells." Cell 22(2): 479-488 (1980).
Chu et al. "SV40 DNA transfection of cells in suspension: analysis of the efficiency of transcription and translation of T-antigen." Gene 13(2): 197-202 (1981).
Edge et al. "Total synthesis of a human leukocyte interferon gene." Nature 292(5825): 756-762 (1981).
Felgner et al. "Lipofection: a highly efficient, lipid-mediated DNA-transfection procedure." Proceedings of the National Academy of Sciences 84(21): 7413-7417 (1987).
Francis et al. "Aspartoacylase supports oxidative energy metabolism during myelination", Journal of Cerebral Blood Flow & Metabolism 32(9): 1725-1736 (2012).
Goodman et al. "Recombinant adeno-associated virus-mediated gene transfer into hematopoietic progenitor cells." Blood 84(5): 1492-1500 (1994).
Graham et al. "A new technique for the assay of infectivity of human adenovirus 5 DNA." Virology 52(2): 456-467 (1973).
Jay et al. "Chemical synthesis of a biologically active gene for human immune interferon-gamma. Prospect for site-specific mutagenesis and structure-function studies." Journal of Biological Chemistry 259(10): 6311-6317 (1984).
Klein et al. "High-velocity microprojectiles for delivering nucleic acids into living cells." Nature 327(6117): 70-73 (1987).
Mannino et al. "Liposome mediated gene transfer." Biotechniques 6(7): 682-690 (1988).
McPhee et al. "Effects of AAV-2-mediated aspartoacylase gene transfer in the tremor rat model of Canavan disease." Molecular Brain Research 135(1-2): 112-121 (2005).
Miller et al. "Redesign of retrovirus packaging cell lines to avoid recombination leading to helper virus production." Molecular and Cellular Biology 6(8): 2895-2902 (1986).
Mitani et al. "Transduction of human bone marrow by adenoviral vector." Human Gene Therapy 5(8): 941-948 (1994).
Moffet et al. "N-Acetylaspartate in the CNS: from neurodiagnostics to neurobiology." Progress in Neurobiology 81(2): 89-131 (2007).
Naldini et al. "In vivo gene delivery and stable transduction of nondividing cells by a lentiviral vector." Science 272(5259): 263-267 (1996).
Pastan et al. "A retrovirus carrying an MDR1 cDNA confers multidrug resistance and polarized expression of P-glycoprotein in MDCK cells." Proceedings of the National Academy of Sciences 85(12): 4486-4490 (1988).
Schwarzenberger et al. "Targeted gene transfer to human hematopoietic progenitor cell lines through the c-kit receptor." Blood 87(2): 472-478 (1996).
Shigekawa et al. "Electroporation of eukaryotes and prokaryotes: a general approach to the introduction of macromolecules into cells." Biotechniques 6(8): 742-751 (1988).
Wolff et al. "Direct gene transfer into mouse muscle in vivo." Science 247(4949): 1465-1468 (1990).

\* cited by examiner

METABOLIC THERAPY FOR OXIDATIVE STRESS IN THE BRAIN THROUGH TARGETED NEURONAL CATABOLISM OF N-ACETYL-ASPARTIC ACID

CROSS REFERENCE TO RELATED APPLICATIONS

This application is a continuation of, and claims priority to, U.S. patent application Ser. No. 15/644,313, filed Jul. 7, 2017, now issued as U.S. Pat. No. 10,391,153, which is continuation of, and claims priority to, U.S. patent application Ser. No. 13/906,171, filed May 30, 2013, now issued as U.S. Pat. No. 9,700,604, which claims priority to U.S. Provisional Application No. 61/653,087, filed May 30, 2012, the contents of all of which are incorporated by reference in their entireties.

FIELD OF THE INVENTION

The present invention relates to a novel method of treatment for treating brain disorders via the catabolism of N-acetylaspartic acid in neurons to support ATP synthesis under conditions of oxidative stress. The invention has applications in the treatment and diagnosis of neurodegenerative disorders such as Alzheimer's disease.

BACKGROUND OF THE INVENTION

The term "neurodegenerative disease" encompasses a broad spectrum of phenotypically distinct pathological entities that are connected superficially by their incidence within the brain. The correct functioning of neural networks in the brain requires the strict maintenance of electrochemical gradients across cell membranes. These gradients are extremely energy-intensive and account for approximately 20% of the body's total energy budget.

The essential function of the brain is to support electrochemical cell-to-cell communication, which is estimated to consume 47% of the ATP derived from the oxidation of glucose, with very little in the way of alternative energy substrates available. This intensive energetic demand places constraints on fundamental aspects of brain function, making it acutely sensitive to energetic compromise. Metabolic stress places an acute demand on this relatively restricted energy source, and if energy use continues to exceed generation, nervous system function will soon be compromised. Oxidative stress of this nature often precedes neuronal death and is a component of practically every known neurodegenerative condition. Therefore, ability to minimize oxidative stress can prove effective in progression of neurodegenerative disorders.

N-acetylaspartic acid (NAA) is the second most abundant neuronal amino acid derivative in the brain. NAA provides for a clinical index of neuronal metabolic integrity across almost the entire spectrum of neurodegenerative diseases on account of its tight association with neuronal metabolic integrity. Reductions in the neuronal amino acid derivatives of NAA constitute a marker of metabolic integrity across almost the entire neuropathological spectrum, suggesting involvement of NAA in a fundamental aspect of metabolic homeostasis. However, despite over 50 years of research, the function of NAA in the context of neurodegenerative disease remains obscure.

The natural NAA metabolic cycle is tightly compartmentalized. Experimental evidence indicates that NAA function is restricted to a role in fatty acid synthesis during developmental myelination. This function is dependent on the hydrolytic enzyme aspartoacylase (ASPA). ASPA cleaves NAA into aspartate and free acetate. In the brain, ASPA is restricted primarily to white matter producing oligodendrocytes, while synthesis occurs almost exclusively in neurons.

Cleavage of NAA into aspartate and free acetate provides an acetylated moiety that is believed to support fatty acid synthesis during developmental myelination. Prior experiments suggest that mitochondria have a central role in many neurodegenerative diseases. As NAA can is as an acetyl donor in the myelin lipid synthesis pathway in oligodendrocytes, via the catabolic activity of the enzyme ASPA, it can play a role in progression of neurodegenerative diseases.

It is also believed that both fatty acid and ATP synthesis require a steady supply of acetyl coenzyme A (AcCoA). The overwhelming majority of AcCoA available in the brain comes directly from the oxidation of glucose. Thus, during the intensive period of developmental myelination, the cleavage of NAA by ASPA in oligodendrocytes uncouples fatty acid synthesis from ATP generation by way of supplementing AcCoA.

It is further believed that loss of ASPA function results in demyelination and spongiform degeneration, leading to neurodegenerative disorders such as the inherited pediatric leukodystrophy Canavan disease (CD). CD is the only disease with known pathology associated with abnormally elevated levels of NAA in the brain. Other neurodegenerative disorders such as Alzheimer disease (AD) also has been the subject of much research. Despite progress in therapy, Alzheimer, remain as a debilitating disease, and no current therapy treats the basic defect of such condition. Although neurodegenerative diseases are invariably multi-factorial, the identification of a common stress response would be of considerable therapeutic benefit.

The ability to redirect metabolic resources from non-essential functions likely forms the basis of maintaining cellular integrity in the face of pathological stress. If ASPA activity was increased in neurons, a novel energetic supplement could be achieved by cleaving millimolar concentrations of NAA at its source to support ATP synthesis. The state of art at this time has not described the use of NAA as a source for ATP synthesis. Therefore there is a need in the art to explore such alternative cellular source of AcCoA as an alternative source for ATP synthesis cascade.

SUMMARY OF THE INVENTION

The present invention addresses the needs of prior art by providing a novel method of producing AcCoA in neurons. In one aspect, the present invention provides a targeted expression of ASPA in neurons using recombinant viral vectors. In another aspect, the present invention relates to a novel method for treating brain disorders and brain injuries associated with energy deficient tissues. The present invention describes for a method of alleviating energy deficiency at local tissues by increasing the catabolism of NAA in neurons. In one embodiment, the catabolism of NAA at the cellular level is accomplished by the enzyme ASPA as an energy-yielding process that can support ATP synthesis by supplying at least one rate limiting substrate such as AcCoA.

In another aspect, the present invention provides for methods of expressing ASPA in neurons, via viral or non-viral methods, to supplement oxidative metabolism. In another aspect of the invention, the expression of ASPA in neurons provides a prophylactic measure for withstanding oxidative stress at respective cellular and tissue levels of patients at risk of developing a wide range of clinically relevant neurological conditions caused by metabolic and oxidative stress.

In another aspect, the present invention relates to methods of treatment for any neurodegenerative condition or injury to the brain or central nervous system including, but not limited to, Alzheimer's disease, Parkinson's disease, stroke, and traumatic brain injury. In yet another aspect of the invention, methods of treating subjects that suffer from or are at risk of developing a neurodegenerative disease are disclosed. Such methods include following the steps of targeting neurons for extraphysiological expression of ASPA by administering therapeutically effective amounts of a ASPA DNA or a delivery construct containing recombinant viral vectors and at least one isolated endogenous or exogenous DNA that codes for the enzyme ASPA or a protein that regulates the intra and extra-cellular activity of ASPA.

In another aspect, the present invention provides novel cellular methods of promoting extra-physiological ATP synthesis by enhancing or potentiating ASPA activity in non-ASPA containing neural cells.

BRIEF DESCRIPTION OF THE FIGURES

(FIG. 4A) levels of NAA were significantly reduced in the brains of AAV-ASPA animals relative to AAV-GFP and Sham surgery controls at 4 months (10 weeks after surgeries; n=6) alongside a significant improvement in GSH: GSSG (FIG. 4B). Note the significant reduction in GSH:GSSG in 5xFAD controls (sham and AAV-GFP) relative to wild type animals. (FIG. 4C) Representative HPLC chromatogram showing the association between lowered NAA and increased GSH in AAV-ASPA brains (black line) as compared to AAV-GFP brains (gray line).

DETAILED DESCRIPTION OF INVENTION AND PREFERRED EMBODIMENTS

Figure 1A:
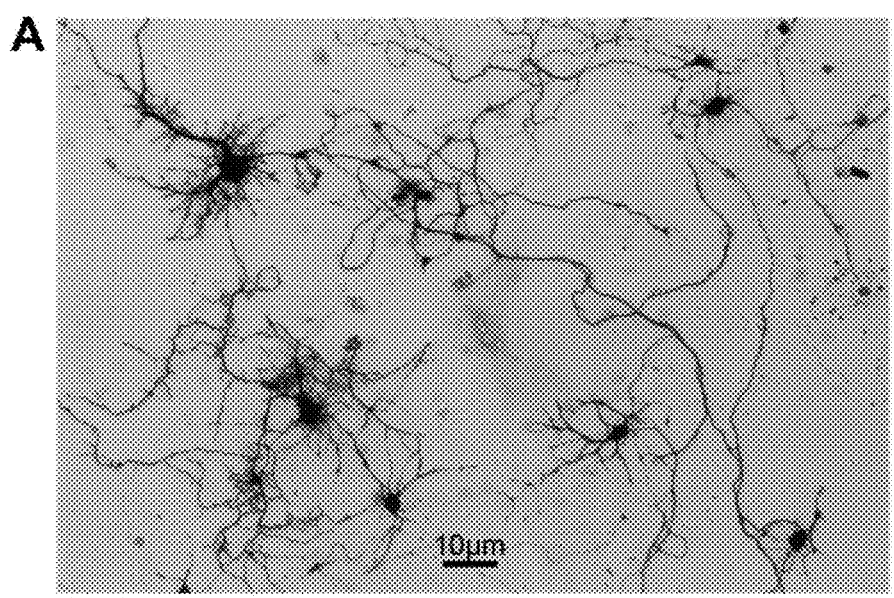
FIGS. 1A-1C provide that expression of ASPA in primary neurons results in increased ATP levels during oxidative stress. Primary cortical neurons were subject to glucose-oxygen deprivation in the presence of NAA (10 mM) and assayed for levels of AcCoA and ATP by HPLC. The results indicated that AAV-ASPA transduced cells (FIG. 1A) manifested significantly greater quantities of both energetic metabolites (FIGS. 1B & 1C) than AAV-GFP negative controls, suggesting increased resistance to oxidative stress.

The present invention provides for a novel method for treating brain disorders associated with oxidative stress. In at least one aspect of the present invention, novel energy-yielding processes are contemplated, whereby the inventors employ the ASPA dependent catabolic conversion of NAA as the pathway to generate rate limiting substrates essential for the synthesis of ATP. In one embodiment, the catabolism of NAA at the cellular level increases the supply of AcCoA substrate which respectively supports ATP synthesis at the site of interest generating additional source of AcCoA for metabolic energy. In another aspect of the present invention, methods of treating subjects in need are described wherein the method provides for expression of ASPA in neurons or any other cells within the nervous system that do not naturally exhibit ASPA expression.

In another aspect of the invention, gene therapy delivery constructs containing an isolated DNA of ASPA (SEQ. ID. No. 1) or DNA for any one of aspartoacylase; aminoacylase II; N-acetylaspartate amidohydrolase; acetyl-aspartic deaminase; acylase II and adenoviral associated virus (AAV) are disclosed. Another aspect of the invention provides for pharmaceutical compositions and methods for treating, preventing or reducing symptoms of neurodegenerative diseases associated with neurodegeneration leading to disorders such as Alzheimer disease (AD), Amyotrophic Lateral Sclerosis (ALS), and the inherited pediatric leukodystrophy Canavan disease (CD).

Another aspect of the invention provides compositions and methods for treatment of CD or AD utilizing transgene expression of ASPA within cells that are either without or are pathophysiologically compromised to express ASPA in sufficient amounts. In one embodiment the ASPA gene to be expressed in the host cells is a naked, wild type or a mutated ASPA gene, or is in the form of an AAV-ASAP delivery construct. In a more preferred embodiment, a viral or non-viral non-immunogenic ASPA containing delivery constructs comprising AAV and an isolated ASPA DNA, is administered to a patient at risk of AD or CD in therapeutically effective amounts to treat or slow down the progression of demyelination at the neuronal level. In a preferred embodiment, the nucleic acid encoding ASPA is operatively lined to a promoter. In another preferred embodiment, the promoter is a cell or tissue-specific promoter, for example, a neuron-specific promoter. Such promoters are known in the art and include, for example, the neuron specific enolase promoter.

In another aspect, methods of augmenting metabolic process can be achieved by additional genetic, pharmacologic and dietary interventions that would enhance local ATP availability via the targeting of NAA in the brain. Additional embodiments for augmenting metabolic process include for example expression of extraphysiological ASPA in neurons, astrocytes or oligodendrocytes (e.g., the expression of ASPA in cholinergic neurons of the Alzheimer's disease brain); expression of extraphysiological Nat8L (NAA synthase) in neurons, astrocytes or oligodendrocytes; administration of pharmacologic agents that alter ASPA or Nat8L expression in neurons, astrocytes or oligodendrocytes; genetic or pharmacologic manipulation of signaling pathways that target NAA synthesis or catabolism in neurons, astrocytes or oligodendrocytes; and manipulation of stem cells for the purpose of modulating NAA synthesis or catabolism (e.g., the ex-vivo expression of ASPA; the ex-vivo synthesis of NAA synthase).

In at least one preferred embodiment, the present invention is supplemented by instituting a dietary regime that target NAA synthesis or catabolism in neurons, astrocytes or oligodendrocytes. Such regime may include administration of anti-oxidants such as vitamin E, vitamin C, flavonoids, herbal polyphenols, suitable carotenoid, ketone therapy, triheptanoin, succinic acid, and calcium acetate.

The natural NAA metabolic cycle is tightly compartmentalized, with synthesis restricted to neurons and catabolism by ASPA to oligodendrocytes. NAA constitutes approximately 1% of the dry weight of the mammalian brain and is present in millimolar quantities, with the overwhelming majority being present intraneuronally. Therefore, the expression of ASPA in neural cells, neurons and astrocytes, via viral or non-viral methods, will have direct access to an abundant supply of substrates that can be used for supplementation of oxidative metabolism in cells that are affected by a wide range of neuronal pathologies.

In at least one aspect of the present invention, the inventors describe an animal model in which ASPA-null transgenic mouse manifest metabolic markers of oxidative stress immediately prior to progressive white matter degeneration. Those of ordinary skill can appreciate that a rise in metabolic markers for oxidative stress, indicates that NAA catabolism plays a central role in the maintenance of metabolic integrity in white matter-producing oligodendrocytes (Francis, et al., 2012). In yet another embodiment, methods and kits for analyzing the concentration of such metabolic markers are described as diagnostic tools for evaluating patient's risk of developing neurodegenerative diseases such as AD or CD.

While ASPA activity is restricted to white matter cells in the brain, the demonstrable ability of extraphysiological levels of ASPA activity to supplement ATP synthesis provides for therapeutic strategies and interventions in brain cells. In at least one aspect of the present invention, mechanism of delivering an ASPA containing construct to tissues and areas that are ASPA null, are at risk of ASPA expression deficiency, or are at risk of experiencing or undergoing oxidative stress.

In at least another embodiment, methods of delivery of a nucleic acid encoding ASPA or a functionally mutated homolog thereof to specific populations of brain cells in vivo are disclosed for generation of free acetate that would respectively support ATP synthesis. In at least another embodiment, methods for increasing the resistance against oxidative stress and subsequently cell death caused by oxidative stress in degenerative neurological conditions associated with demyelination are described.

In another aspect of the invention, recombinant cells are described that are transformed with the expression of a nucleic acid encoding ASPA or a functionally mutated homolog thereof with at least 75%, 85%, 90%, or 95% homology. In such embodiment, the nucleic acid encoding ASPA is introduced into host cells of interest through direct delivery or by a construct comprising AAV and a nucleic acid encoding ASPA (SEQ ID NO: 1) or a functional fragment thereof in wild form or a functionally mutated homolog, wherein the nucleic acid codes an amino acid sequence of (SEQ ID NO: 2) or operatively linked to a promoter. In another embodiment, the recombinant cells are isolated and prepared for administration into a subject or cultured and cultivated in vitro for future use. Suitable cells include a mammalian cell, preferably human neurons, astrocytes, oligodendrocytes or ASPA-deficient oligodendrocytes. In another aspect of the invention, methods of producing cellular AcCoA are described by taking steps that include (a) culturing host cells that are transformed with the expression of nucleic acid encoding ASPA through a delivery mechanism, (b) isolating a population of cells showing an elevation in ASPA concentration and (c) administering such population of cells in a pharmaceutically acceptable carrier to a patient at risk of developing a neurodegenerative disease such as AD or CD. The delivery mechanism can include the delivery of a construct consist of AAV and a nucleic acid encoding ASPA (SEQ. ID. No: 1) or a functional fragment thereof, and wherein the nucleic acid codes for an amino acid sequence of (SEQ. ID. No: 2) or an operatively linked peptide to a promoter under conditions that promote expression of said ASPA.

The adeno-associated virus (AAV) is a single-stranded DNA parvovirus, which integrates into a host genome during the latent phase of infectivity. AAV is considered a dependent virus because it requires helper functions from either adenovirus or herpes-virus in order to replicate. In the absence of either of these helper viruses, AAV can infect cells, uncoat in the nucleus, and integrate its genome into the host cell chromosome, but cannot replicate or produce new viral particles. AAVs are described to be useful as transducing vectors, in part, because none of the known serotypes have been linked to any human disease. This feature renders the AAVs distinct from autonomous parvoviruses, which can cause a variety of human disorders. The suitable sereotypes include but are not limited to AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV. In a more preferred embodiment such vectors are an AAV1 vector, an AAV2 vector, an AAV3 vector, an AAV4 vector, an AAV5 vector, an AAV6 vector, an AAV7 vector, an AAV8 vector, an AAV9 vector, an AAV 10 vector, or an AAV11 vector.

The present invention also contemplates the use of other viral or non-viral vectors and delivery constructs that can facilitate ASPA gene delivery to the tissue or the area of interest. The delivery constructs described herein include, "vector construct," "expression vector," and "gene transfer vector," or any other nucleic acid construct capable of directing the expression of a gene of interest and which can transfer gene sequences to target cells. For such reasons, any delivery construct for purposes of the present invention include viral or non-viral constructs that do not provoke immunogenic response, have broad host range, excellent safety profile and the duration of transgene expression in infected hosts can be a candidate for the presently described delivery mechanisms. In at least one embodiment, other viral vectors include but are not limited to a retroviral vector, an alphaviral vector; a vaccinia viral vector; an adenoviral vector, and an herpes simplex viral vector. In another embodiment, the non-viral vector include but are not limited to a lipid, a poly-lysine, a synthetic polyamino polymer, or a plasmid.

As used herein, the terms "gene transfer," "gene delivery," and "gene transduction" refer to methods or systems for reliably inserting a particular nucleotide sequence (e.g., DNA) into targeted cells. This mechanism can include not only naked, or wild type isolated DNA for ASPA, but also any homolog thereof with at least 75%, 80%, 85%, 90%, 95% or 98% homology.

As used herein, the term "gene therapy" refers to a method of treating a patient wherein nucleic acid sequences are transferred into cells of a patient such that activity and/or the expression of a particular molecule, polypeptide, protein, or enzyme is restored or initiated.

The term "nucleic acid" as used herein refers to a DNA or RNA sequence. Nucleic acids can, for example, be single or double stranded. The term includes sequences such as any of the known base analogues of DNA and RNA. The term "recombinant DNA molecule" refers to a DNA molecule which is comprised of segments of DNA joined together by means of molecular biological techniques. The term "regulatory element" refers to a genetic element which can control the expression of nucleic acid sequences. For example, a promoter is a regulatory element that facilitates the initiation of transcription of an operably linked coding region. Other regulatory elements are splicing signals, termination signals, etc.

Those of the ordinary skill in the art can appreciate that the inventors provide for methods of treatments that can be used in management of various neurodegenerative disorders. These diseases can be hereditary and/or sporadic conditions which are characterized by progressive nervous system dysfunction and are often associated with atrophy of the affected central or peripheral structures, demyelination and plaque formation within the nervous system. They include diseases such as Alzheimer's disease and other dementias, Brain Cancer, Degenerative Nerve Diseases, Encephalitis, Epilepsy, Genetic Brain Disorders, Head and Brain Malformations, Hydrocephalus, Stroke, Parkinson's disease, Multiple Sclerosis, Amyotrophic Lateral Sclerosis (ALS or Lou Gehrig's Disease), Huntington's Disease, Prion Diseases, Traumatic Brain Injury and others. The pathophysiological tissues afflicted by such condition includes but is not limited to the cerebral cortex; intracranial white matter, basal ganglia, thalamus, hypothalamus, brain stem, and cerebellum.

Alzheimer's disease (AD) manifests a decline in the integrity of neural networks that are involved in learning and memory and is the major age-related neurodegenerative disease. Currently no effective treatment for AD exists. Over and above age, known risk factors for AD are few, but cholinergic sensory neurons feature prominently in the disease. These neurons synthesize acetylcholine (ACh) via an energy-intensive process that is glucose-dependent, and requires AcCoA. Acetylcholine synthesis is reduced in AD and cholinergic defects precede plaque formation in mutant B-amyloid mouse models of AD.

ACh has significant parallels with NAA in that both are acetylated derivatives that require tricarboxylic acid (TCA) cycle intermediates for synthesis. ACh synthesis is supported by the recycling of choline and acetate from the synaptic cleft via acetylcholinesterase (AChE), which breaks ACh down into constituent choline and acetate for readsorbtion by the presynaptic terminal. Acetate is then available for the synthesis of AcCoA, which in turn contributes to both ACh and ATP.

Figure 3:
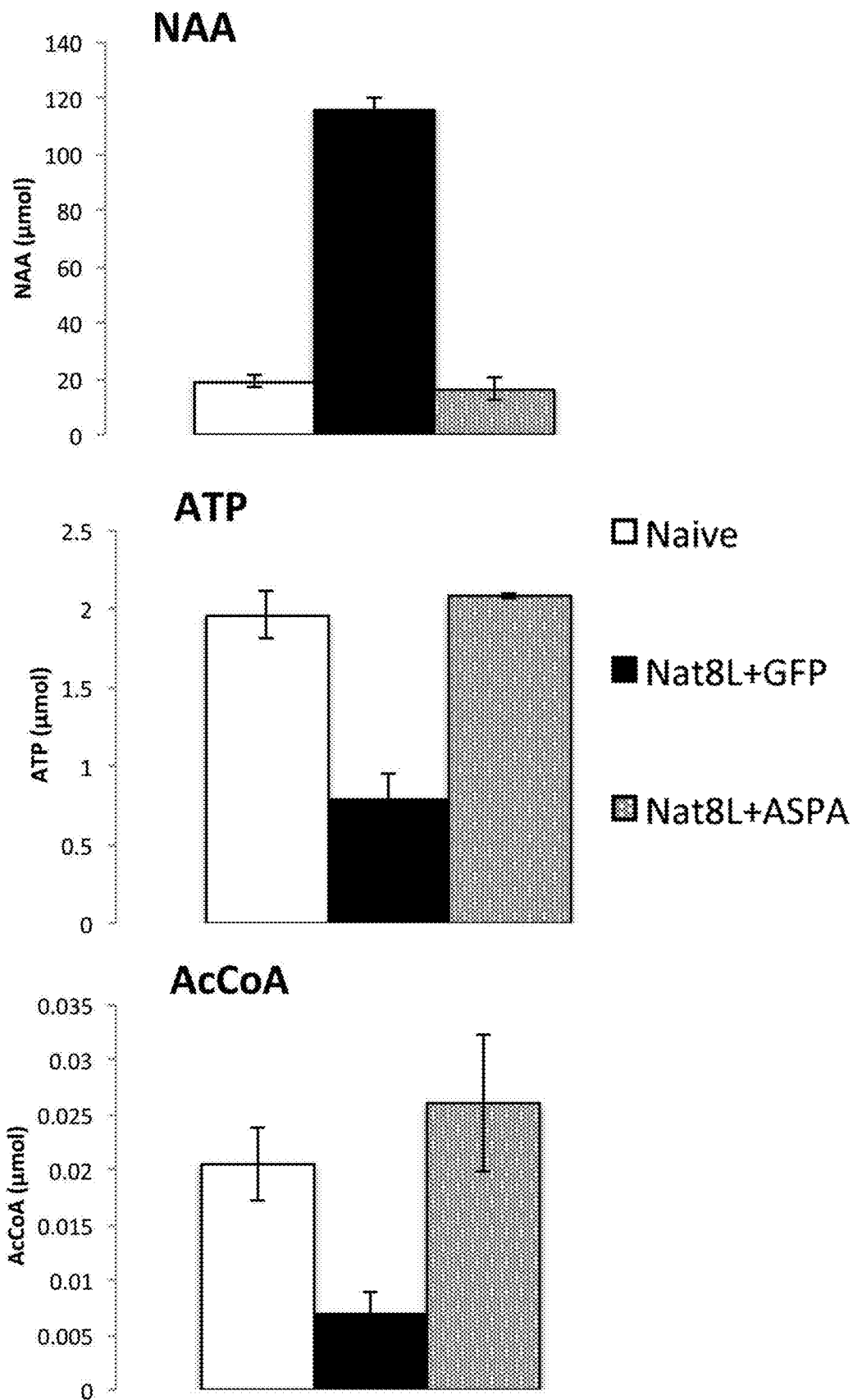
FIG. 3 provides a generally applicable demonstration of the energetic cost of NAA synthesis and the potential for energetic augmentation by ASPA. HEK-293 cells were transfected with plasmid DNA containing expression cassettes for either NAA synthase (Nat8L), ASPA, or both. Overexpression of Nat8L results in large increases in NAA, as measured by HPLC, and corresponding reductions in both AcCoA and ATP. Expression of ASPA in Nat8L-transfected cells reverses the energetic deficit associated with NAA synthesis by increasing levels of AcCoA and ATP.

The present inventors have generated efficacy data in a mouse model of familial AD by transducing cholinergic neurons with adeno-associated viral vectors containing ASPA (AAV-ASPA). The data support the energetic demands of ACh synthesis through the provision of extra-physiological levels of AcCoA (FIG. 3). The term "in operable combination," "in operable order," or "operably linked" refers to the linkage of nucleic acid sequences in such a manner that a first nucleic acid molecule (e.g., promoter) is capable of directing the transcription of a second nucleic acid sequence (e.g., siDNA).

The term "treating" or "treatment" as used herein refers to executing a protocol, which may include administering one or more drugs to a patient (human or otherwise), in an effort to alleviate signs or symptoms of the disease. Alleviation can occur prior to signs or symptoms of the disease appearing as well as after their appearance. Thus, "treating" or "treatment" includes "preventing" or "prevention" or "prophylactically treating" a disease. In addition, "treating" or "treatment" does not require complete alleviation of signs or symptoms, does not require a cure, and specifically includes protocols that have only a marginal effect on the patient.

The term "patient" or "subject" in need refers to a biological system to which a treatment can be administered for the added clinical benefit. A biological system can include, for example, a human patient, mammals such as mice, rodents, dogs, cat as well as other animals such as fish, birds, etc.

Treatment of defects in the brain cells or tissues afflicted by any neurodegenerative disease, involving demyelination and/or brain atrophy, can be reversed by the methods disclosed in this invention. Tissue specific treatment is another aspect of the present invention by which tissues of cells void of ASPA can ex vivo or in vivo be treated to express nucleic acid encoding ASPA. In another aspect of the present invention, expression of ASPA will lead to enhance catabolism of NAA and increase concentrations of AcCoA, a substrate for metabolic pathway. In particularly preferred embodiments, the AAD-ASPA with a suitable promoter displays excellent expression in neuron cells of a mammal indicating the reversal of neurodegenerative manifestations.

As defined herein, a "therapeutically effective amount" or "therapeutic effective dose" is an amount or dose of AAV-ASPA DNA constructs capable of producing sufficient amounts of a desired protein to restore or reinitiate the activity of the ASPA, thus providing substrates to accelerate the ATP synthetic pathway. A therapeutically effective amount or dose of transfected AAV construct that confer expression of human ASPA, for example, to a patient suffering from AD or CD will decrease the symptoms of AD and/or CD. Additionally, a therapeutically effective amount or dose of transfected AAV gene therapy construct which provides expression of human ASPA or an active portion thereof will treat, prevent or prophylactically treat any further damage to the central nervous system, brain cells, or other tissues affected by such conditions.

Cells of the subject useful for cultivation and/or administration include all cells within the nervous system regardless of the type or location. Accordingly, such cells can be from any three nerve types; nerves motor neurons, sensory neurons and autonomic neurons and locations such as cerebral cortex; intracranial white matter, basal ganglia, thalamus, hypothalamus, brain stem, and cerebellum.

AAV gene therapy vectors and constructs of the present invention can be made using known techniques in the art to provide, as operably linked components, (a) control sequences including transcriptional initiation and termination regions and (b) nucleotide sequences encoding a desired protein or a functional fragment thereof. Suitable viral vector for the delivery of the ASPA nucleic acid include but are not limited to AAV serotypes 1, 2, 3, 4, 5, 6, 7, 8, 9, 10 or 11, preferably AAV2. In one embodiment, suitable vectors include virus vectors (e.g., retrovirus, alphavirus; vaccinia virus; adenovirus, adeno-associated virus, or herpes simplex virus), and non-viral vectors such as lipid vectors, poly-lysine vectors, synthetic polyamino polymer vectors that are used with nucleic acid molecules, plasmids, and the like.

In another embodiment suitable viral vectors include, but are not limited to vectors derived from: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Geminivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picornaviridae; Plasmaviridae; Prodoviridae; Polydnaviridae; Potexvirus group; Potyvirus; Poxviridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and Plant virus satellites.

Those of ordinary skill in the art would appreciate protocols that are used for producing recombinant viral vectors and for using viral vectors for nucleic acid delivery can be found. Such protocols can be found for example in *Current Protocols in Molecular Biology*, Ausubel, F. M., et al. (eds.) Greene Publishing Associates, (1989) and other standard laboratory manuals (e.g., Vectors for Gene Therapy. In: *Current Protocols in Human Genetics*. John Wiley and Sons, Inc.: 1997).

In another aspect of the present invention, vectors employed in the methods of this invention may be for example a plasmid, a nonviral vector or a viral vector, such as a retroviral vector which can package a recombinant retroviral genome (see e.g., Pastan et al., *Proc. Natl. Acad. Sci. U.S.A.* 85:4486 (1988); Miller et al., *Mol. Cell. Biol.* 6:2895 (1986)). In this aspect of the invention the recombinant retrovirus can be used to infect and thereby deliver a nucleic acid of the invention to the infected cells. The exact method of introducing the altered nucleic acid into mammalian cells is, of course, not limited to the use of retroviral vectors. Other techniques are widely available for this procedure including the use of adenoviral vectors (Mitani, et al., *Hum. Gene Ther.* 5:941-948, 1994), adeno-associated viral (AAV) vectors (Goodman, et al., *Blood* 84:1492-1500, 1994), lentiviral vectors (Naldini, et al., *Science* 272:263-267, 1996), pseudotyped retroviral vectors (Agrawal, et al., *Exper. Hematol.* 24:738-747, 1996).

Also included in the present invention are chimeric viral particles, which are well known in the art and contain viral proteins and/or nucleic acids from two or more different viruses in any combination to produce a functional viral vector. Chimeric viral particles of this invention can also comprise amino acid and/or nucleotide sequence of non-viral origin (e.g., to facilitate targeting of vectors to specific cells or tissues and/or to induce a specific immune response).

The present invention also provides "targeted" virus particles (e.g., a parvovirus vector comprising a parvovirus capsid and a recombinant AAV genome, wherein an exogenous targeting sequence has been inserted or substituted into the parvovirus capsid).

Physical transduction techniques can also be used as a mode of delivery of the ASPA nucleic acid sequence. Such techniques include but are not limited to liposome delivery and receptor-mediated and other endocytosis mechanisms (see, for example, Schwartzenberger, et al., *Blood* 87:472-478, 1996). Other appropriate means for transfection, including viral vectors, chemical transfectants, or physicomechanical methods such as electroporation and direct diffusion of DNA, are described, for example, in Wolff, et al., *Science* 247:1465-1468, (1990); and Wolff, *Nature* 352:815-818, (1991).

Recombinant proteins may also be expressed utilizing the methods of the present invention. The nucleic acid sequences encoding the ASPA gene or portion thereof can be fused in frame, with respect to the translational reading frame, with nucleic acid sequences encoding tags or epitopes. Such tags and/or epitopes are used routinely by skilled practitioners to track protein expression and as means to purify recombinant proteins. The tags may be useful for detecting the expression of the transgene after administration.

Nucleic acid sequences coding for the above-described proteins may be obtained using recombinant methods, such as by screening cDNA and genomic libraries from cells expressing proteins or by deriving the sequence from a vector known to include the same. Furthermore, the desired sequence may be isolated directly from cells and tissues containing the same, using standard techniques, such as phenol extraction and PCR of cDNA or genomic DNA. Nucleotide sequences encoding a protein of interest may also be produced synthetically, rather than cloned. For example, the complete sequence may be assembled from overlapping oligonucleotides prepared by standard methods and assembled into a complete coding sequence (See e.g., Edge, Nature 292:756 (1981); Nand Jay, et al., J. Biol. Chem., 259:6311 (1984)).

Although it is not intended that the present invention be limited to any particular methods for assessing the production of biologically active proteins or assess capability of molecules that can modulate the activity of ASPA and NAA catabolism, such methods as immunoassays, and biological activity assays in vitro and in vivo are also contemplated.

The following is an exemplary embodiment of the present invention wherein nucleic acid sequences encoding ASPA is produced and administered to a host. One of skill in the art would appreciate that nucleic acid sequences encoding other proteins of interest may be incorporated into the AAV gene therapy vectors of the present invention.

In another aspect of the present invention, the described constructs herein can be introduced into a cell or tissue of interest using standard methodology known to those of skill in the art (e.g., transfection). A number of transfection techniques are generally known in the art (See e.g., Graham, et al., Virol., 52:456 (1973), Sambrook, et al. supra, Davis, et al., supra, and Chu, et al., Gene 13:197 (1981)). Particularly suitable transfection methods include calcium phosphate co-precipitation (Graham, et al., Virol., 52:456-467 (1973)), direct micro-injection into cultured cells (Capecchi, Cell 22:479-488 (1980)), electroporation (Shigekawa, et al., BioTechn., 6:742-751 (1988)), liposome-mediated gene transfer (Mannino, et al., BioTechn., 6:682-690 (1988)), lipid-mediated transduction (Feigner, et al., Proc. Natl. Acad. Sci. U.S.A. 84:7413-7417 (1987)), and nucleic acid delivery using high-velocity microprojectiles (Klein, et al., Nature 327:70-73 (1987)).

In another aspect of the present invention, ex vivo cell cultures or populations having suitable host cells are contemplated for delivery of ASPA, AAV-ASPA construct or other functional moieties or variations thereof. Such cell cultures can include non-allergenic microorganisms, yeast cells, insect cells, meshenchymal cells, undifferentiated cells, mammalian cells or stem cells, that may be, or have been, used as recipients of a heterologous DNA molecule. Thus, as indicated above, a host cell or producer cell refers to a cell which has been transfected with an exogenous DNA sequence and are capable of expressing ASPA and/or administration to a patient of subject.

AAV-ASPA gene therapy constructs may be administered to any tissue suitable for expression of proteins or fragments thereof. In a preferred embodiment, the AAV gene therapy particles of the present invention are in combination with a suitable pharmaceutical carrier. The compositions may be administered alone or in combination with at least one other agent, such as a stabilizing compound, which may be administered in any sterile, biocompatible pharmaceutical carrier. The pharmaceutical compositions may also contain other active substances, precursors, drugs, antioxidants, immune suppressants or hormones. Examples of active substances include anti-inflammatory agents, immune suppressants, or hormones. In another embodiment, the present method include the administration or co-application of an adjunct immunotherapy, a dietary treatment, or combinations thereof to alleviate potential side effects profiles associated with the present invention. Alternatively, the pharmaceutical compositions of the invention may be injected using a conventional syringe, although other delivery methods such as convection-enhanced delivery are envisioned.

In preferred embodiments, the pharmaceutical compositions contain pharmaceutically acceptable excipients. Such excipients or carriers include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol.

Pharmaceutically acceptable salts can also be included therein, for example, mineral acid salts such as hydrochlorides, phosphates, sulfates, and the like; and the salts of organic acids such as acetates, propionates, benzoates, and the like. Additionally, auxiliary substances, such as wetting or emulsifying agents, pH buffering substances, and the like, may be present in such vehicles. An exemplary pharmaceutical preparation may be a lyophilized powder which may contain any or all of the following: 1-50 mM histidine, 0.1%-2% sucrose, and 2-7% mannitol, at a pH range of 4.0 to 6.5. A thorough discussion of pharmaceutically acceptable excipients is available in Remington's Pharmaceutical Sciences (Mack Pub. Co., 20th Edition, Easton, Pa. (2005)).

Modes of administration include oral, suppositories, and transdermal applications. Therapeutic doses of AAV-ASPA or biologically active portions thereof will depend on, among other factors, the age and general condition of the subject, and the severity of the disease. Thus, a therapeutically effective amount in humans will fall in a relatively broad range that may be determined based on the result of clinical trials and the response of individual patients to treatment.

The present invention also provides a novel method of treatment for treating brain disorders associated with oxidative stress. As set forth previously, the inventors propose herein that the catabolism of NAA by the enzyme ASPA is an energy-yielding process that can support ATP synthesis through the supply of substrates for the cellular metabolic energy cascade. The natural NAA metabolic cycle is tightly compartmentalized, with synthesis restricted to neurons and catabolism by ASPA to oligodendrocytes. In the preferred embodiment, the proposed treatment provides for novel strategies to introduce ASPA to neural cells, neurons, astrocytes specifically, where it is not naturally found.

ASPA is normally found in oligodendrocytes, while NAA is synthesized exclusively in neurons. Neurons do not have the ability to catabolized NAA. NAA constitutes approximately 1% of the dry weight of the mammalian brain and is present in millimolar quantities, with the overwhelming majority being present intraneuronally. In at least one aspect of the present invention, the inventors show that the expression of ASPA in neurons, via viral or non-viral methods, has direct access to an abundant supply of substrate for the supplementation of oxidative metabolism in cells affected by a wide range of neuronal pathologies.

In another aspect of the present invention a reduction in early signs of oxidative stress under the claimed methodology is achieved. In yet another embodiment, the present methodology shows a long term treatment for conditions that attribute to learning deficiencies and/or progressive cognitive decline.

ACh is synthesized from choline and AcCoA by choline acetyltransferase (ChAT). After being released by presynaptic neurons, ACh is rapidly broken down to choline and acetate, which are taken up by the presynaptic terminal. In at least one embodiment, the acetate supplements ACh synthesis by forming AcCoA. AcCoA is then available for either ACh, or ATP synthesis via the TCA cycle. Providing cholinergic neurons with the means to catabolize endogenous NAA via transduction with AAV-ASPA supports both ACh and ATP synthesis.

Figures 1B, 1C:
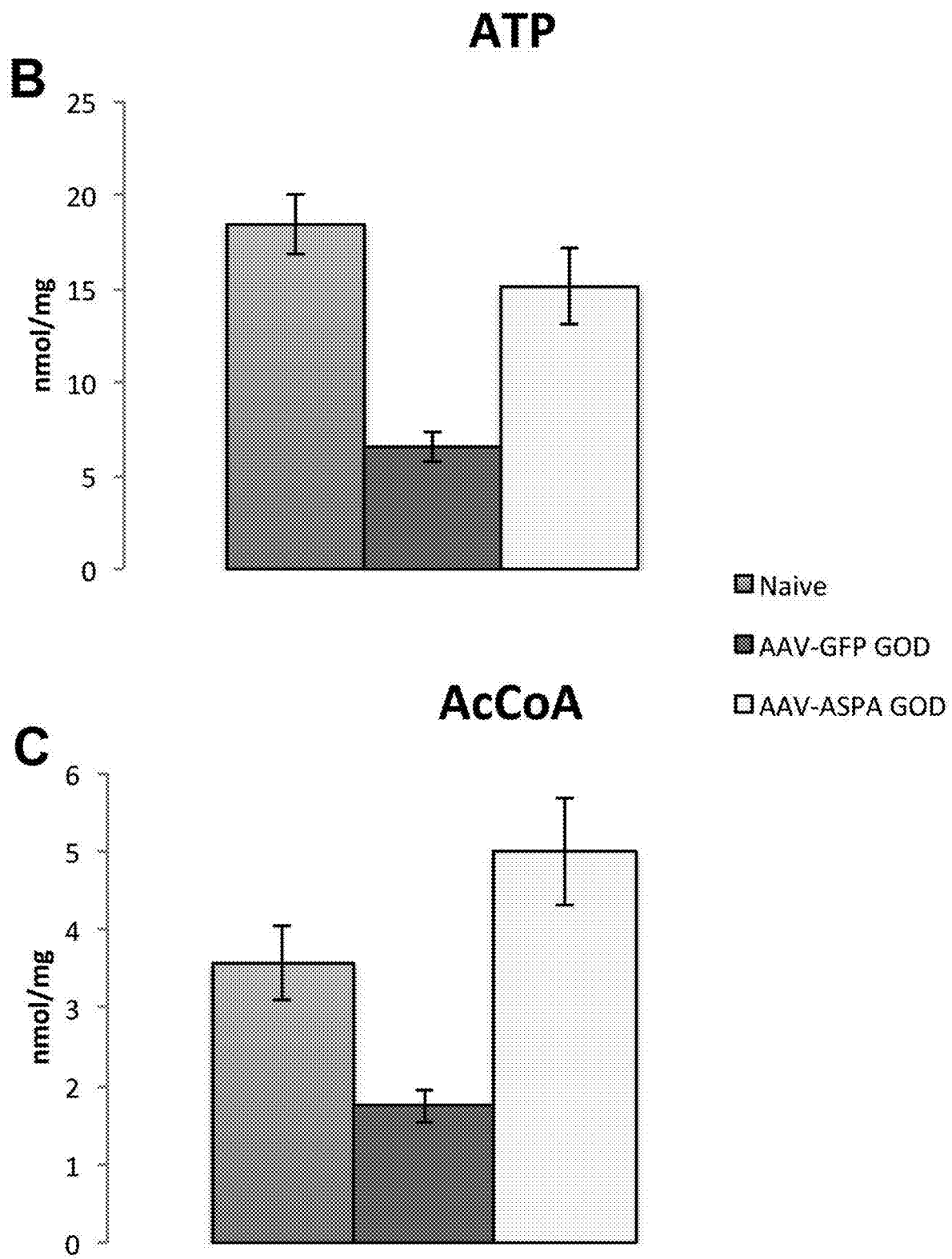
Figure 2:
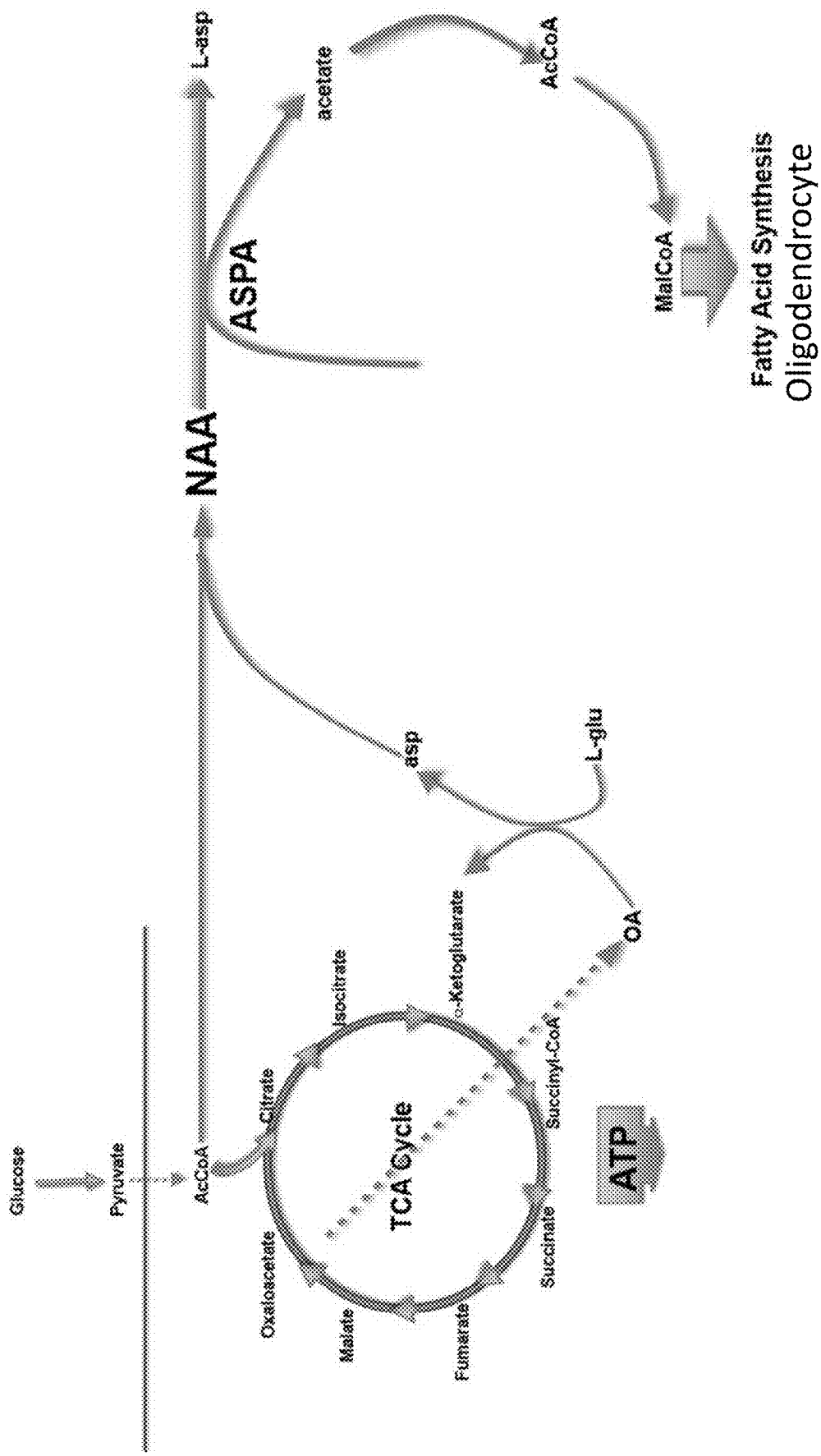
FIG. 2 provides the natural compartmentalization of NAA synthesis and catabolism in the brain and the relationship of NAA metabolism to energy. NAA synthesis in neurons draws on TCA cycle metabolites, specifically AcCoA. NAA is exported to oligodendrocytes, which contain ASPA, for the generation of acetate to support myelination (fatty acid synthesis). The present invention describes the use of viral vectors for introducing ASPA in neurons to supplement cellular levels of AcCoA through the liberation of acetate from NAA molecules. The transferal of ASPA to the neuronal compartment would therefore result in a net gain of ATP.

The present inventors have expressed ASPA in primary neurons in culture and provided resistance to glucose/oxygen deprivation that can be quantified in increased levels of ATP (FIGS. 1A-1B). Depriving neurons of glucose and oxygen for a brief period of time replicates conditions experienced by neurons in vivo during hypoxia-ischemia in vivo. An insult of this nature deprives the brain of the glucose and oxygen required for generating energy to maintain ionic gradients required for normal synaptic function.

In at least one preferred embodiment, increased cellular ASPA activity to provide extraphysiological levels of ATP is translated to greater functional capacity under stress. As oxidative stress is a component of practically every neurodegenerative condition and brain injury known, those of ordinary skill in the art can appreciate that patients suffering or are at risk of developing neurodegenerative diseases can benefit from the presently contemplated invention.

One application of the present invention is in patients at risk of developing Alzheimer's disease. Such patients, for example, manifests an oxidative deficit and associated lipid and protein damage in areas of the brain associated with B-amyloid plaques and neurofibrillary tangles. In Parkinson's disease, the apparent selective vulnerability of dopaminergic neurons to respiratory stress is associated with significant mitochondrial abnormalities in this discrete neuronal population. Both of these neurodegenerative conditions are amenable to targeted gene delivery with viral vectors, and both would benefit from oxidative support provided by the supplementation of Tri-carboxylic acid (TCA) cycle intermediates via the catabolism of NAA by ASPA.

As indicated herein, the TCA cycle is the main conduit to metabolic energy in the brain and utilizes glucose to generate ATP. NAA synthesis is closely coupled to the TCA cycle in neurons, and the acetylation of aspartate draws on AcCoA from the TCA cycle (see FIG. 3). Acetylated aspartate, in the form of NAA, is then transported out of the neuron and into white matter producing oligodendrocytes. Catabolism of NAA by ASPA in oligodendrocytes yields AcCoA for fatty acid synthesis, thereby allowing the TCA cycle in these cells to continue unabated. The synthesis and export of NAA by is therefore energy intensive for the neuron. The energetic balance maintained by NAA synthesis and catabolism can be readily demonstrated in any cell type by genetic intervention (FIGS. 1A-1B & FIG. 3). Thus, overexpression of the rate limiting NAA synthetic enzyme, Nat8L, results in an increase in NAA (FIG. 3), a drop in AcCoA (FIG. 3), and a corresponding drop in ATP (FIG. 3). Metabolic deficits resulting from extraphysiological levels of NAA synthesis are rescued by overexpression of ASPA. Thus, NAA synthesis is energy-intensive, while NAA catabolism is energy yielding.

Because the TCA cycle is a fundamental component of all neuronal processes, the proposed technology is applicable to the entire neuropathological spectrum, from acute injury through to complex neurocognitive phenotypes.

EXAMPLES

It should be appreciated that the invention should not be construed to be limited to the examples that are now described; rather, the invention should be construed to include any and all applications provided herein and all equivalent variations within the skill of the ordinary artisan.

1. Improved Oxidative Integrity in 5xFAD Mice Treated With AAV-ASPA

The 5xFAD mouse is a model of inherited AD. It contains 5 mutations in genes found clinically that result in the accumulation of B-amyloid fragments in the brain. This animal manifests 13-42 amyloid-positive plaques in the brain and an associated learning deficit from approximately 4 months of age onwards. This learning deficit can be assayed for by the use of a maze apparatus that measures spatial working memory.

Figure 4A:
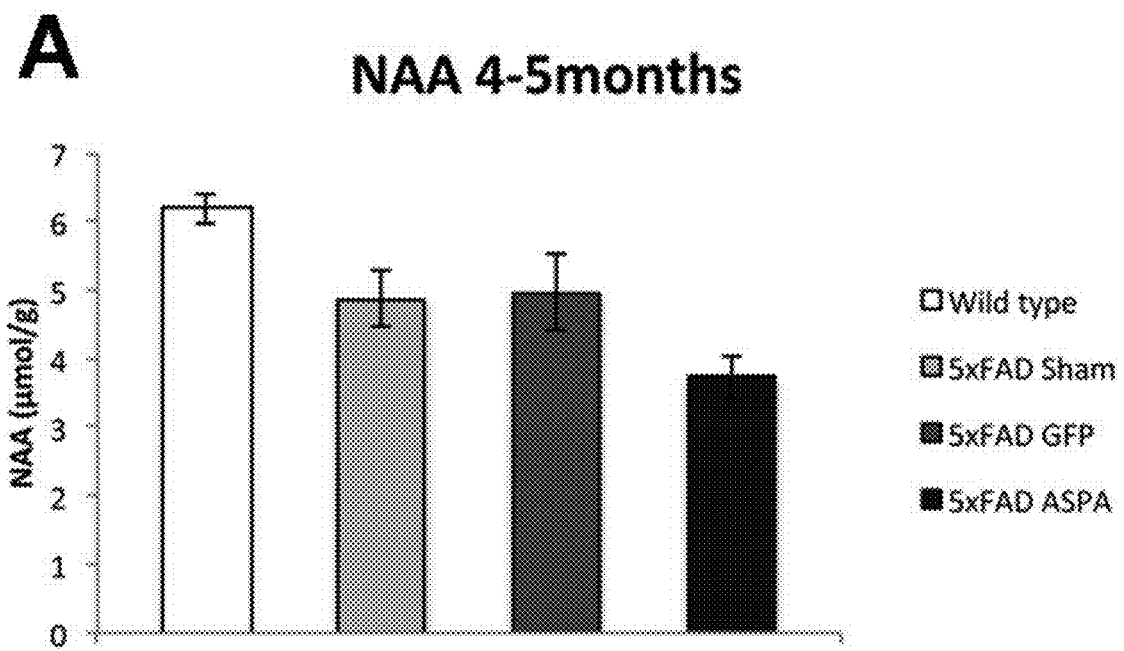
FIGS. 4A-4C depict the effects of Transduction of 5xFAD mice with AAV-ASPA on oxidative integrity. 6 week old animals were transduced with AAV-ASPA and brains analyzed at 4 months of age for NAA and GSH:GSSG relative to sham surgery, AAV-GFP and wild type controls.
Figure 4B:
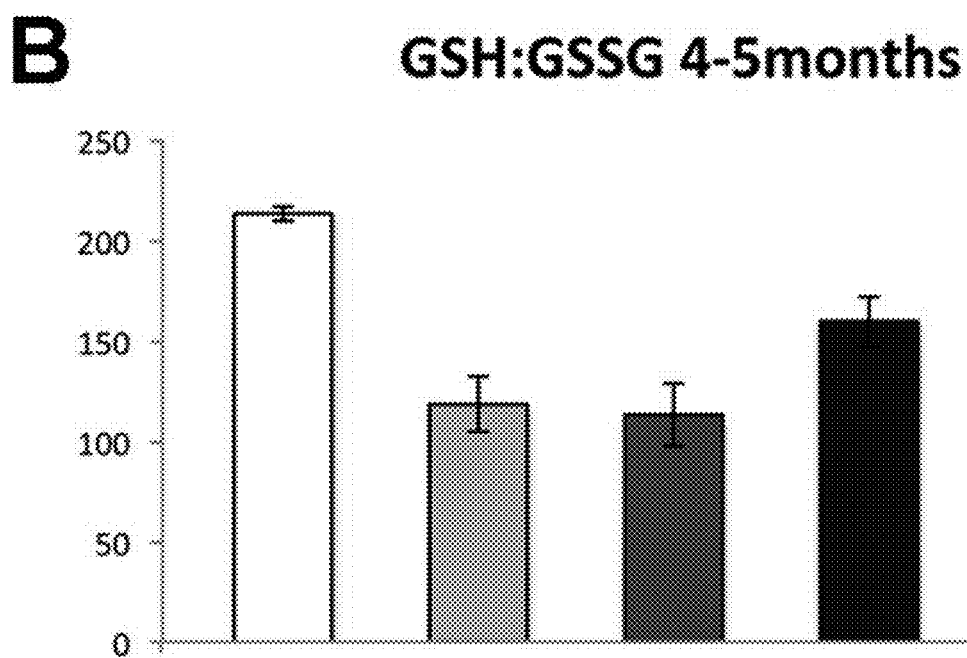
Figure 4C:
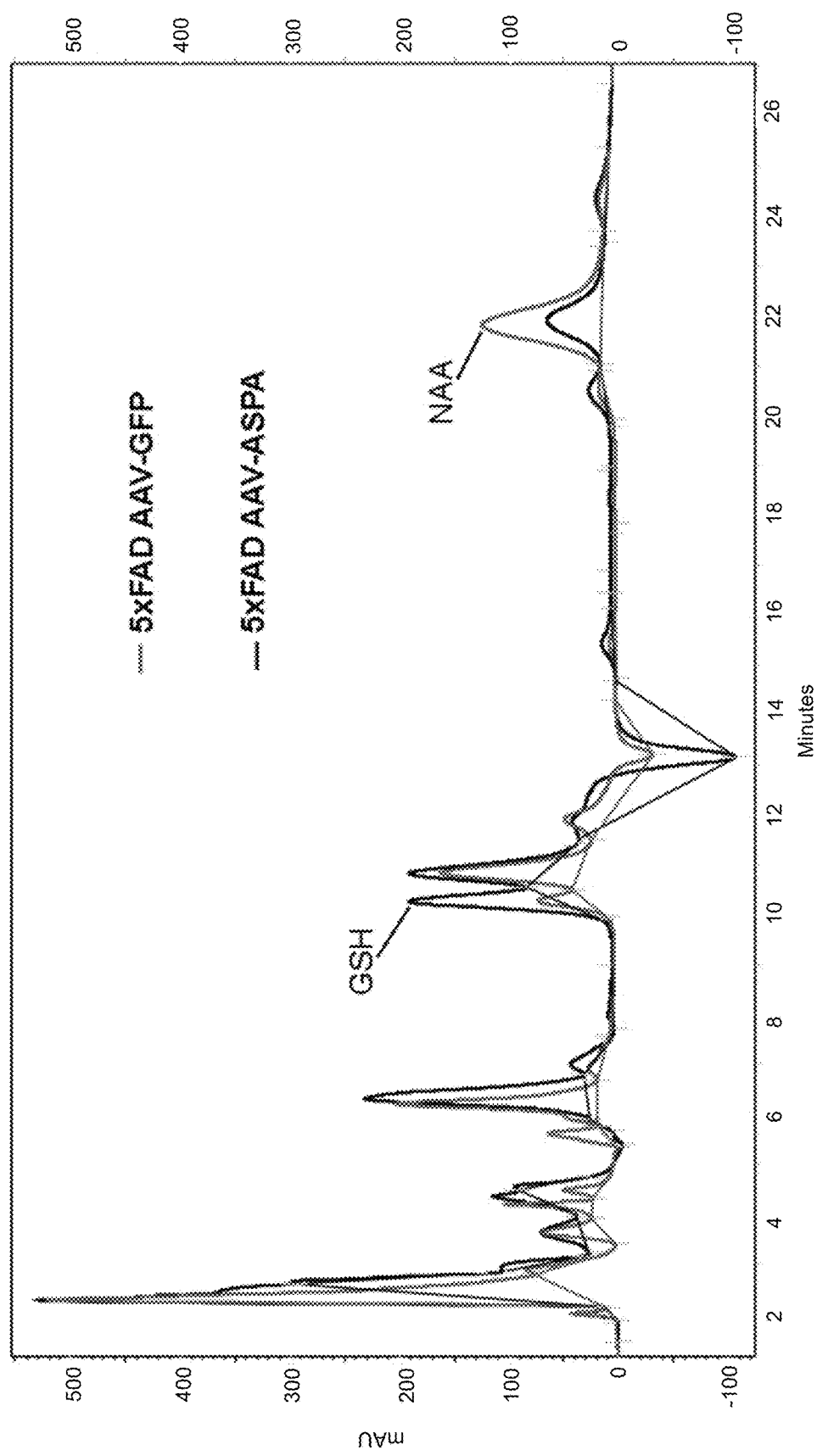

5xFAD mice were injected with AAV-ASPA at 6 weeks of age, and brains analyzed for ASPA activity (i.e., lowered endogenous NAA) and markers of oxidative stress at 4 months of age (FIGS. 4A-4C). Expression of ASPA in neurons of 5xFAD mice resulted in a significant reduction in endogenous NAA. It should be noted that NAA is the second most abundant molecule in the brain, and even when abnormally low, is in the millimolar quantities.

2) Rescue of Age-Related Cognitive Phenotype in AAV-ASPA-Treated 5xFAD Mice

Figure 5:
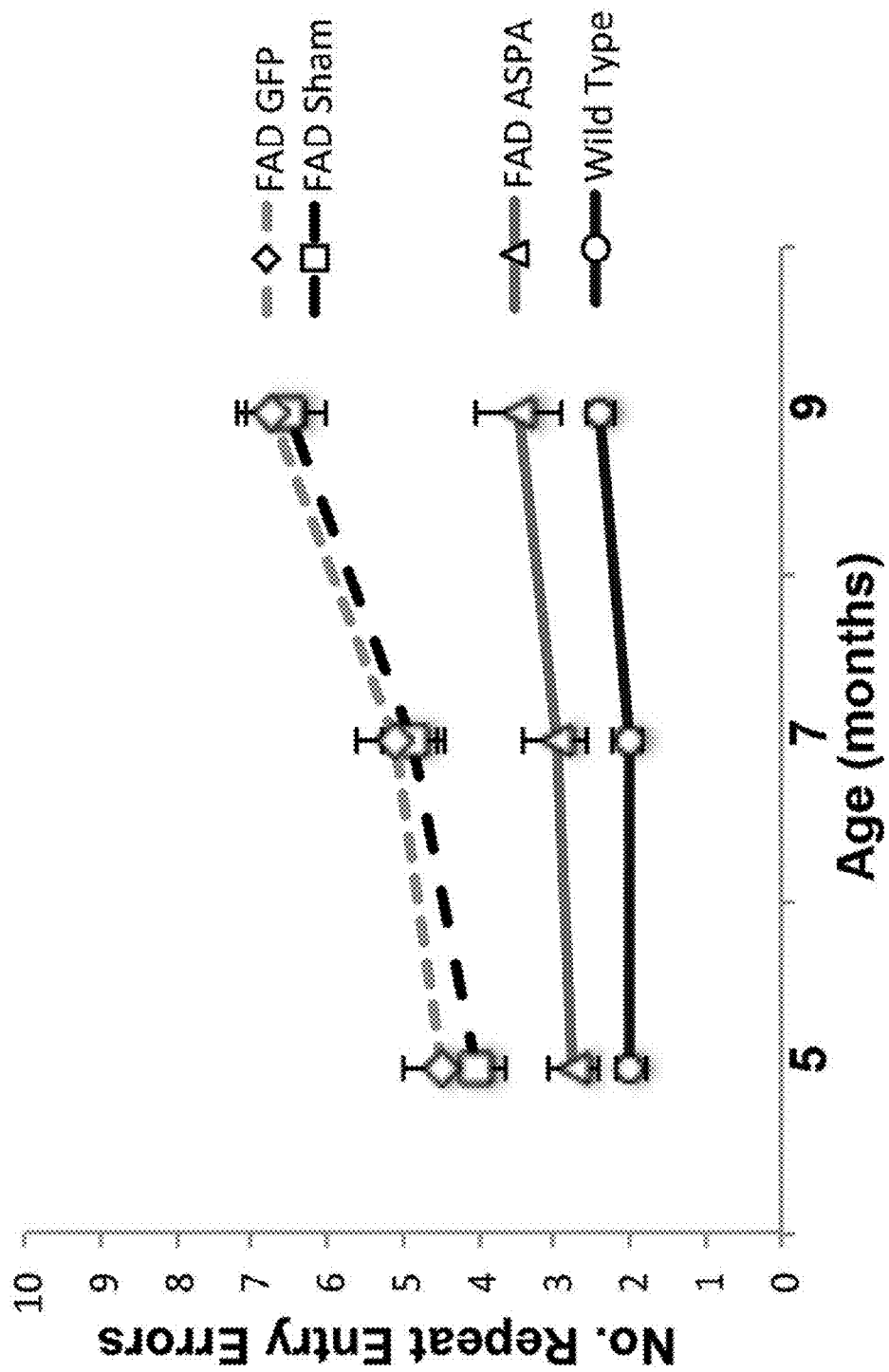
FIG. 5 provides memory testing in 5xFAD mice at 5, 7 and 9 months of age. In this scenario, mice were injected with either AAV-ASPA, AAV-GFP (a non-functional green fluorescent protein) or with physiological saline (Sham) at 6 weeks of age. At 5, 7 and 9 months of age, the animals were then tested in the 8-arm radial maze along with age-matched normal, non-FAD mice (Wild Type). The number of entries into previously visited arms (repeat entries) prior to completion of the task (visiting all arms) is the variable being measured. Normal mice make few errors at all time points relative to 5xFAD AAV-GFP and Sham controls. 5xFAD AAV-ASPA mice exhibited highly significant reductions in error counts at all ages tested (red group), indicating long term improvements in memory.
Figure 6:
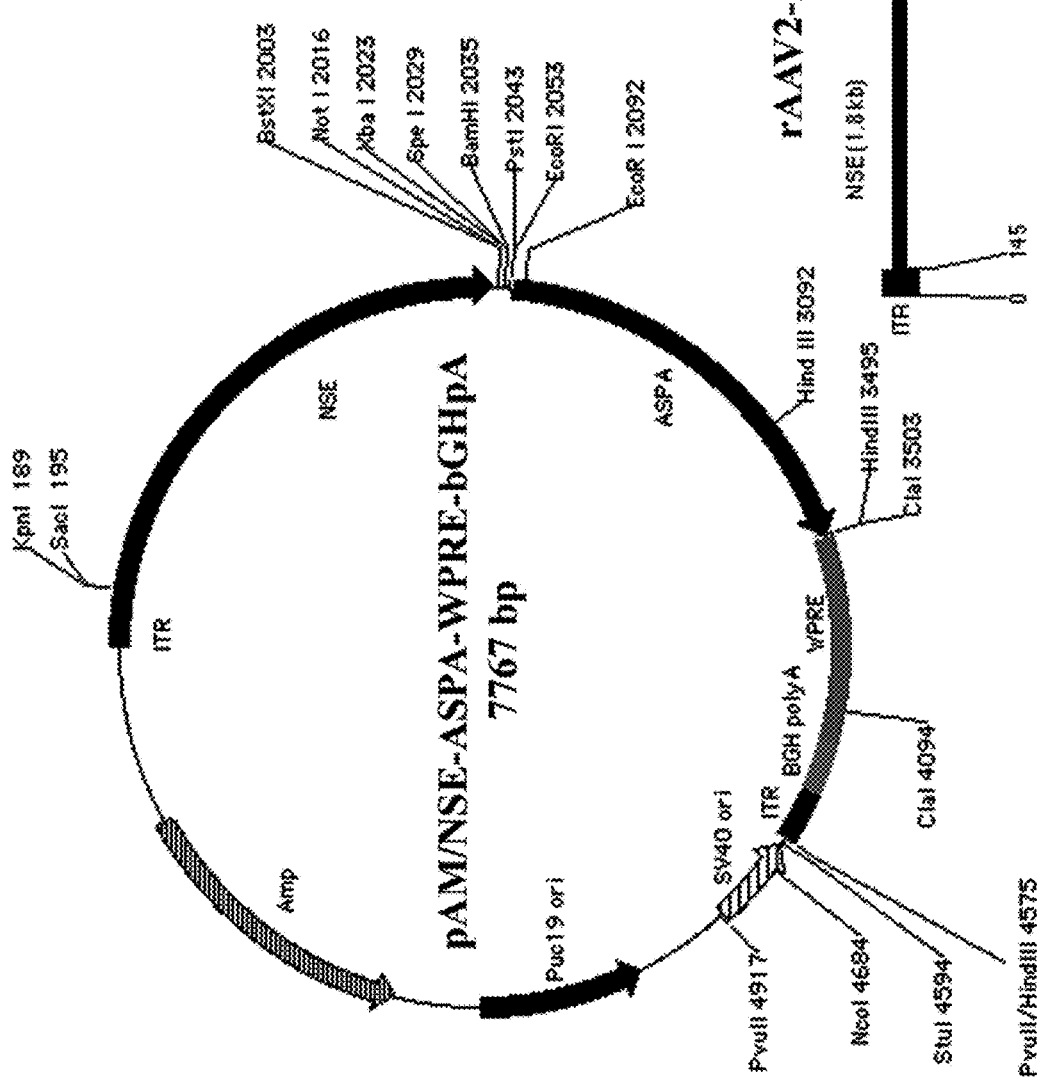
FIG. 6 provides the AAV-ASPA expression cassette. The AAV plasmid map shows the components of the ASPA transgene cassette. The elements circumscribed by the ITRs are packaged into AAV 2 virions as shown.
Figure 7:
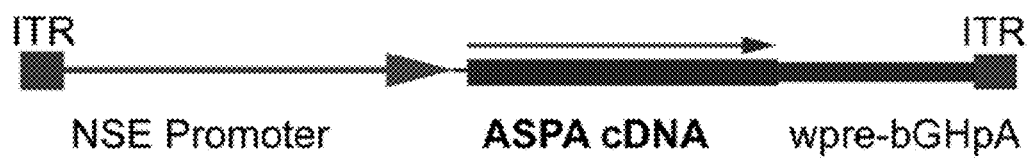
FIG. 7 provides the components of each ssDNA unit that is packaged inside the AAV capsid; the rAAV Transcription Cassette. The manufacturing of rAAV2-NSE-ASPA-WPRE-bGH is further described. Accordingly, the AAV transcription cassette consisted of a 1.8 kb rat neuron-specific enolase (NSE) promoter flanking the ASPA cDNA, at the 5' end and woodchuck hepatitis virus post-translational regulatory element (WPRE) and bovine growth hormone polyA (bGHpA) sequences flanking the cDNA at the 3' end, with the cassette bounded by AAV2 ITR sequences. In this embodiment, recombinant AAV was produced by transient transfection of HEK 293 cells followed by harvesting and purification involving heparin sulfate affinity column chromatography. The final formulation was as recombinant AAV2-NSE-ASPA-WPRE-bGHpA, in IX phosphate-buffered saline.

In this example, memory testing in animals began when they were 5 months old. Animals were habituated to a maze with 8 arms radiating from a central platform. Animals were trained to search for food rewards at the end of each arm, and the successful retrieval of rewards from all 8 arms constitutes a completed test. If an animal re-visits an arm from which it has already taken food, an error is recorded. As 5xFAD mice age, the number of these errors increases, reflective of the degeneration of the associated memory circuits. When tested at 5, 7 and 9 months of age, 5xFAD mice treated with AAV-ASPA exhibited highly significant reductions in the numbers of errors made over the testing period, indicating the long term recovery of working memory (see FIG. 5.)

3) Dramatic Reduction in the Levels of β42 Amyloid Plaques in AAV ASPA-Treated 5xFAD Mice Ages Mice are being maintained up until 9 months of age, and are currently undergoing testing for this time point. A few 9 month animals have been generated, and the brains of these animals are currently being analyzed for histopathology. 5xFAD AAV-ASPA brains that have been analyzed thus far appear to have dramatic reductions in the levels of β42 amyloid plaques. Thus, the observed rescue of a major cognitive deficit (FIG. 5) to correlates with reductions in AD-like pathology.

All publications cited in the specification, both patent publications and non-patent publications are indicative of the level of skill of those skilled in the art to which this invention pertains. All these publications are herein fully incorporated by reference to the same extent as if each individual publication were specifically and individually indicated as being incorporated by reference. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method of reducing oxidative stress in a subject suffering from Parkinson's disease, the method comprising:
   (a) identifying a subject suffering from Parkinson's disease; and
   (b) administering to the subject an effective amount of a formulation comprising an isolated nucleic acid comprising a first sequence that encodes aspartoacylase (ASPA) under conditions whereby the nucleic acid is expressed in a host cell of the subject and whereby expression of ASPA leads to enhanced catabolism of NAA, increased concentration of AcCoA, and reduced oxidative stress.

2. The method of claim 1, wherein the host cell is a nerve cell selected from the group consisting of oligodendrocytes, neurons, astrocytes, and any combination thereof.

3. The method of claim 1, further comprising administration of a secondary therapeutic product selected from the group consisting of an antibody, a cultured cell, an active substance and a diagnostic agent.

4. The method of claim 1, wherein the formulation further comprises a pharmaceutically acceptable carrier.

5. The method of claim 1, further comprising a step of administering an adjunct immunotherapy, a dietary regime, or combinations thereof.

6. The method of claim 1, wherein the isolated nucleic acid is in a vector and operatively linked to a promoter.

7. The method of claim 6, wherein the vector is an AAV vector comprising a regulatory element.

8. The method of claim 7, wherein the AAV vector is an AAV 2 vector.

9. The method of claim 8, wherein the AAV2 vector further comprises bovine growth hormone polyA, the promoter is neuron specific enolase, and the regulatory element is woodchuck hepatitis virus post-translational regulatory element.

10. The method of claim 1, wherein the first sequence that encodes ASPA is SEQ ID NO: 1.

11. A method for improving the disease phenotype of a subject suffering Parkinson's disease, the method comprising administering to the subject an effective amount of a formulation comprising an isolated nucleic acid comprising a first sequence that encodes ASPA under conditions whereby the nucleic acid is expressed in a host cell of the subject and whereby expression of ASPA leads to enhanced catabolism of NAA, increased concentration of AcCoA, and reduced oxidative stress, wherein the formulation is administered to a tissue afflicted by the disease.

12. The method of claim 11, wherein the isolated nucleic acid further comprises a second sequence that encodes a tag and is fused in frame with the first sequence.

13. The method of claim 11, wherein the tissue is selected from the group consisting of cerebral cortex, intracranial white matter, basal ganglia, thalamus, hypothalamus, brain stem, and cerebellum.

14. The method of claim 11, wherein the first sequence that encodes ASPA is SEQ ID NO: 1.

* * * * *

SEQUENCE LISTING

<160> NUMBER OF SEQ ID NOS: 2

<210> SEQ ID NO 1
<211> LENGTH: 1435
<212> TYPE: DNA
<213> ORGANISM: Artificial
<220> FEATURE:
<223> OTHER INFORMATION: Synthetic

<400> SEQUENCE: 1

```
ttgtaacaga aaattaaaat atactccact caagggaatt ctgtactttg ccctttgggt      60
aaagtctcat ttacatttct aaacctttct taagaaaatc gaatttcctt tgatctctct     120
tctgaattgc agaaatcaga taaaaactac ttggtgaaat gacttcttgt cacattgctg     180
aagaacatat acaaaaggtt gctatctttg gaggaaccca tgggaatgag ctaaccggag     240
tatttctggt taagcattgg ctagagaatg gcgctgagat tcagagaaca gggctggagg     300
taaaaccatt tattactaac cccagagcag tgaagaagtg taccagatat attgactgtg     360
acctgaatcg cattttttgac cttgaaaatc ttggcaaaaa aatgtcagaa gatttgccat     420
atgaagtgag aagggctcaa gaaataaatc atttatttgg tccaaaagac agtgaagatt     480
cctatgacat tattttttgac cttcacaaca ccacctctaa catggggtgc actcttattc     540
ttgaggattc caggaataac ttttttaattc agatgtttca ttacattaag acttctctgg     600
ctccactacc ctgctacgtt tatctgattg agcatccttc cctcaaatat gcgaccactc     660
gttccatagc caagtatcct gtgggtatag aagttggtcc tcagcctcaa ggggttctga     720
gagctgatat cttggatcaa atgagaaaaa tgattaaaca tgctcttgat tttatacatc     780
atttcaatga aggaaaagaa tttcctcccct gcgccattga ggtctataaa attatagaga     840
aagttgatta cccccgggat gaaaatggag aaattgctgc tatcatccat cctaatctgc     900
aggatcaaga ctggaaacca ctgcatcctg gggatcccat gttttttaact cttgatggga     960
agacgatccc actgggcgga gactgtaccg tgtaccccgt gtttgtgaat gaggccgcat    1020
attacgaaaa gaaagaagct tttgcaaaga caactaaact aacgctcaat gcaaaaagta    1080
ttcgctgctg tttacattag aaatcacttc cagcttacat cttacacggt gtcttacaaa    1140
ttctgctagt ctgtaagctc cttaagagta gggttgtgcc ttattcaact gcatacatag    1200
ctcctagcac agtgccttat tcggtaggca tctaagcaaa tttcttaaat taattaatat    1260
atctttaaag atatcatatt ttatgtatgt agcttattca aagaagtgtt tcctatttct    1320
atatagtttta ttatacatga tacttgggta gctcaacatt cttaataaac agcctttgta    1380
ttcagaatat aaaattgaaa tagatatata taaagttaaa aaaaaaaaaa aaaaa          1435
```

<210> SEQ ID NO 2
<211> LENGTH: 313
<212> TYPE: PRT
<213> ORGANISM: Artificial
<220> FEATURE:
<223> OTHER INFORMATION: Synthetic

<400> SEQUENCE: 2

```
Met Thr Ser Cys His Ile Ala Glu Glu His Ile Gln Lys Val Ala Ile
1               5                   10                  15

Phe Gly Gly Thr His Gly Asn Glu Leu Thr Gly Val Phe Leu Val Lys
            20                  25                  30

His Trp Leu Glu Asn Gly Ala Glu Ile Gln Arg Thr Gly Leu Glu Val
        35                  40                  45
```

-continued

```
Lys Pro Phe Ile Thr Asn Pro Arg Ala Val Lys Lys Cys Thr Arg Tyr
    50                  55                  60

Ile Asp Cys Asp Leu Asn Arg Ile Phe Asp Leu Glu Asn Leu Gly Lys
65                  70                  75                  80

Lys Met Ser Glu Asp Leu Pro Tyr Glu Val Arg Arg Ala Gln Glu Ile
                85                  90                  95

Asn His Leu Phe Gly Pro Lys Asp Ser Glu Asp Ser Tyr Asp Ile Ile
                100                 105                 110

Phe Asp Leu His Asn Thr Thr Ser Asn Met Gly Cys Thr Leu Ile Leu
                115                 120                 125

Glu Asp Ser Arg Asn Asn Phe Leu Ile Gln Met Phe His Tyr Ile Lys
    130                 135                 140

Thr Ser Leu Ala Pro Leu Pro Cys Tyr Val Tyr Leu Ile Glu His Pro
145                 150                 155                 160

Ser Leu Lys Tyr Ala Thr Thr Arg Ser Ile Ala Lys Tyr Pro Val Gly
                165                 170                 175

Ile Glu Val Gly Pro Gln Pro Gln Gly Val Leu Arg Ala Asp Ile Leu
                180                 185                 190

Asp Gln Met Arg Lys Met Ile Lys His Ala Leu Asp Phe Ile His His
            195                 200                 205

Phe Asn Glu Gly Lys Glu Phe Pro Pro Cys Ala Ile Glu Val Tyr Lys
    210                 215                 220

Ile Ile Glu Lys Val Asp Tyr Pro Arg Asp Glu Asn Gly Glu Ile Ala
225                 230                 235                 240

Ala Ile Ile His Pro Asn Leu Gln Asp Gln Asp Trp Lys Pro Leu His
                245                 250                 255

Pro Gly Asp Pro Met Phe Leu Thr Leu Asp Gly Lys Thr Ile Pro Leu
                260                 265                 270

Gly Gly Asp Cys Thr Val Tyr Pro Val Phe Val Asn Glu Ala Ala Tyr
            275                 280                 285

Tyr Glu Lys Lys Glu Ala Phe Ala Lys Thr Thr Lys Leu Thr Leu Asn
    290                 295                 300

Ala Lys Ser Ile Arg Cys Cys Leu His
305                 310
```